United States Patent [19]

Heinecke

[11] Patent Number: 4,917,928
[45] Date of Patent: Apr. 17, 1990

[54] FOLDED ADHESIVE FILM DRESSING

[75] Inventor: Steven B. Heinecke, New Richmond, Wis.

[73] Assignee: Minnesota Mining and Manufacturing Company, St. Paul, Minn.

[21] Appl. No.: 279,365

[22] Filed: Dec. 2, 1988

[51] Int. Cl.$^4$ ............................ B32B 7/06; B32B 7/12
[52] U.S. Cl. ........................................ 428/41; 428/40; 428/124; 428/130
[58] Field of Search .................................. 428/40–42, 428/124, 130

[56] References Cited

U.S. PATENT DOCUMENTS

| | | | |
|---|---|---|---|
| 3,018,881 | 1/1962 | Wall | 206/56 |
| 3,349,765 | 10/1967 | Blanford | 128/132 |
| 4,050,121 | 9/1977 | Richman | 24/73 VA |
| 4,127,132 | 11/1978 | Karami | 128/287 |
| 4,413,621 | 11/1983 | McCracken et al. | 128/156 |
| 4,513,739 | 4/1985 | Johns | 128/156 |
| 4,598,004 | 7/1986 | Heinecke | 428/40 |
| 4,614,183 | 9/1986 | McCracken et al. | 128/132 R |
| 4,706,662 | 11/1987 | Thompson | 128/155 |
| 4,781,293 | 11/1988 | Johns | 206/441 |
| 4,815,457 | 3/1989 | Mazars et al. | 128/155 |

Primary Examiner—Alexander S. Thomas
Attorney, Agent, or Firm—Donald M. Sell; Walter N. Kirn; Dale A. Bjorkman

[57] ABSTRACT

An adhesive composite delivery system is provided which comprises two liner pieces and a backing folded in such a manner that the composite may be applied in simple motions. The invention is of particular benefit in applications of very thin films such as high moisture vapor permeable films widely used as medical dressings.

19 Claims, 3 Drawing Sheets

FOLDED ADHESIVE FILM DRESSING

FIELD OF THE INVENTION

The present invention relates to pressure-sensitive adhesive composites comprising a backing coated on one surface with adhesive. More particularly, it relates to pressure-sensitive adhesive composites having improved means for handling and application to a surface. The invention is of particular benefit in the application of backings which are very thin, adhesive-coated transparent films widely used as medical dressings.

BACKGROUND

Although the present invention is useful in any adhesive composite needing a delivery system, it has particular benefit in connection with transparent film dressings and surgical drapes. These dressings and drapes are widely used as a protective layer over a wound, facilitating healing in a moist environment while acting as a barrier to liquids and bacteria. Dressings of this type are available under trade names such as Tegaderm TM (3M, St. Paul, Minn.), Bioclusive TM (Johnson & Johnson, New Brunswick, N.J.), Op-Site TM (T. J. Smith & Nephew, Hull, England) and Uniflex TM (Howmedica, Largo, Fla.).

The polymeric films used in such dressings are conformable. By this it is meant that these films are extremely thin, flimsy, and supple. They are supplied with a releasable protective liner overlying the adhesive coated surface of the film. When the liner is removed, the adhesive coated film tends to wrinkle and stick to itself, interfering with the smooth aseptic application of the dressing or drape to the skin. Various delivery systems have been proposed to obviate this problem.

One such delivery system utilizes a three-part liner configuration. U.S. Pat. No. 4,614,183 describes a composite having a relatively thin polymeric film that is releasably adhered to two liner sections with a center gap between the liners. These two liner sections have short J-folds located next to the center gap. A third liner piece covers the center gap on the adhesive coated surface of the backing and extends beyond the J-folds for easy removal. To apply this dressing, the user must first remove the center liner piece, apply the center region of the backing to the substrate, and then reach under the side portions of the dressing to grasp the J-folds and remove the liner pieces from the backing.

U.S. Pat. No. 3,018,881 discloses a folded adhesive bandage package unit having at least three liner pieces and where the adhesive-coated surface of the backing contacts the inside surface of the covering panels. This package has finger tabs that are pulled apart by the user, unfolding the bandage for application to the skin. The package forming panels are separated from the adhesive bandage after application to the skin by continued pulling of the finger tabs.

U.S. Pat. No. 4,050,121 discloses a linerless diaper tab which is folded around the diaper in a "Y configuration" to provide added strength in gripping the diaper. The portion of the tab that is used to fasten the diaper is wrapped around the edge of the diaper and releasably adhered to the anchoring portion of the tab for storage before use. U.S. Pat. No. 4,127,132 discloses a disposable diaper tape fastener wherein the tape tab is folded onto itself and may be unfolded two or more times to expose fresh adhesive. In at least one configuration, the tape strip is maintained in a folded configuration by a suitable means such as a spot of adhesive.

SUMMARY OF THE INVENTION

An adhesive composite is provided having a backing coated on one surface with an adhesive and having first and second liner pieces. The backing has a center region and two side regions adjacent to the center region. The first liner piece is releasably adhered to one of the side regions of the backing and the second liner piece is releasably adhered to the other side region of the backing. The backing is folded around the first liner piece, releasably adhering the center region of the backing to one of the liner pieces. Most preferably, the backing is folded a second time in the opposite direction (back onto itself) in a generally "Z" shaped configuration when viewed on edge, so that the non-adhesive coated surfaces of the center region contacts or is proximate to the non-adhesive coated surface of one of the side regions of the backing.

In a more preferred embodiment, each of the liner pieces has an upper portion and a lower portion that are joined along one edge. These upper and lower liner portions are provided by folding a single piece of liner material (so that the fold becomes an edge) or by joining two separate portions of liner material with an adhesive or by heat sealing so that the portions are attached at one coterminous edge. The two separate portions are joined only at one end so that the opposite ends of the upper and lower liner portions of the liner pieces can be grasped independently. Each of the portions of the liner pieces thus have outward facing and inward facing surfaces. The outward facing surface of the upper portion of the first liner piece is releasably adhered to one of the side regions and the outward facing surface of the upper portion of the second liner piece is releasably adhered to the other side region, each liner piece being oriented so that the edge joining the upper and lower portions abuts the center region of the backing. The backing is folded along a line corresponding to the edge of the first liner piece, releasably adhering the center region of the backing to the outward facing surface of the lower portion of the first liner piece. Most preferably, the backing is folded twice, once along a line corresponding to the edge of the first liner piece as described above and a second time in the opposite direction (back onto itself) along a line corresponding to the edge of the second liner piece. As a result of this second fold, the non-adhesive-coated surfaces of the center region contacts or is proximate to the non-adhesive coated surface of one of the side regions of the backing.

The adhesive composite of this invention can be applied to a substrate by simple motions with a minimum amount of handling of the backing. In the most preferred embodiment, the upper and lower portions of the first liner piece are grasped by the user with one hand, and the upper and lower portions of the second liner piece are grasped with the other hand. The liner pieces are pulled in radially opposite directions, exposing the adhesive-coated center region of the backing through this motion. The center region is applied to the substrate and the lower portions of the first and second liner pieces are pulled in radially opposite directions to expose the adhesive-coated surface of the backing and simultaneously apply the backing to the substrate.

The backing is preferably an adhesive coated film which is permeable to moisture and vapor and should transmit moisture vapor. When a high moisture vapor permeable film is used, the adhesives are preferably biocompatible. Most preferably the pressure-sensitive adhesive composite comprises high moisture vapor permeable film, a high moisture vapor permeable biocompatible adhesive and is transparent.

The liner may be comprised of any conventional liner material which preferably has been coated with a release agent, such as silicone.

DETAILED DESCRIPTION

Figure 1:
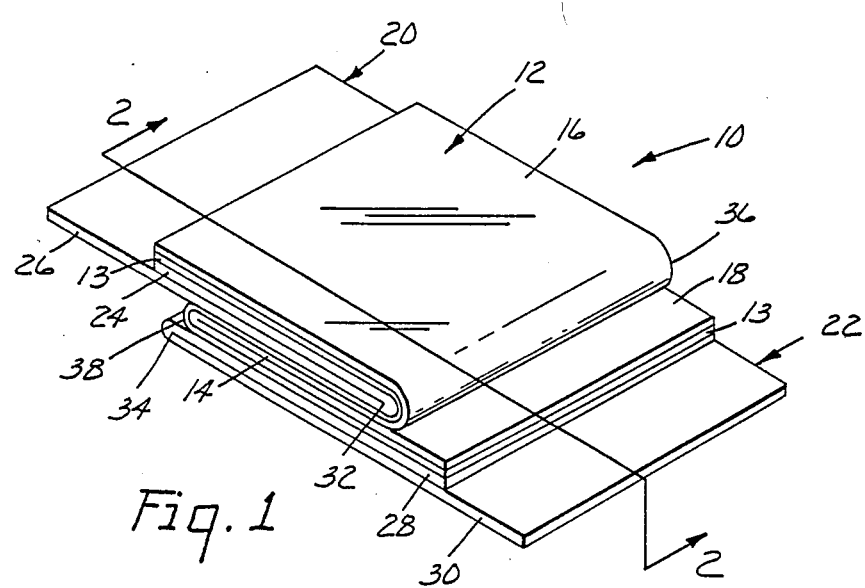
FIG. 1 is a perspective view of a film dressing according to the present invention.
Figure 2:
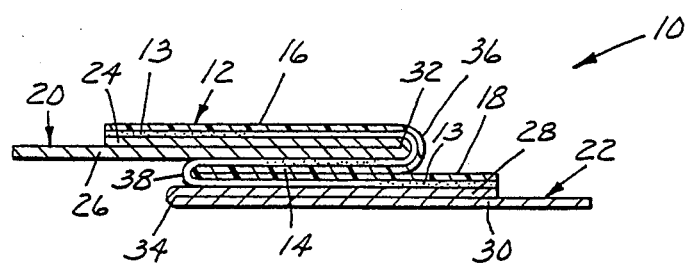
FIG. 2 is a cross-sectional view of the film dressing of FIG. 1 taken along line 2—2.

FIGS. 1, 2, 3a, 3b and 3c show dressing composite 10 of the present invention wherein like numerals refer to like parts of the embodiment. FIG. 1 shows a perspective view of dressing 10. FIG. 2 is a cross-sectional view of dressing 10 taken along line 2—2 of FIG. 1 so that the individual layers may be more readily distinguished. Backing 12 is made of a thin transparent, polymeric film which is moisture vapor permeable and liquid and bacteria impermeable such as a polyester or polyurethane film. Pressure sensitive adhesive 13 is an adhesive exhibiting low irritation to skin, preferably a hypoallergenic acrylate copolymer bioadhesive. Pressure sensitive adhesive 13 covers a least a portion of backing 12 and is here illustrated to cover an entire surface of backing 12. Backing 12 contains center region 14 and side regions 16 and 18. Preferably, the total area of center region 14 is less than the total area of each of side regions 16 and 18 for easier handling during application of the dressing to the skin. The adhesive coated surface of backing 12 is releasably adhered to first liner piece 20 and second liner piece 22.

As may be seen in FIG. 2, first liner piece 20 is divided into upper portion 24 and lower portion 26 by the fold in the backing that forms edge 32 joining the liner portions. Similarly, second liner piece 22 is divided into upper portion 28 and lower portion 30 by the fold that forms edge 34 joining the liner portions. Upper portion 24 of first liner piece 20 is releasably adhered to side region 16 of backing 12 and upper portion 28 of second liner piece 22 is releasably adhered to side region 18 of backing 12. Backing 12 is folded at fold 36 so that center region 14 is releasably adhered to lower portion 26 of first liner piece 20. Backing 12 is then folded back onto itself at fold 38 so that the backing is in a generally Z-shaped conformation. Preferably, backing 12 is folded at fold 38 such that second liner piece 22 overhangs the adhesive coated surface of backing 12. Because of this overhang, the adhesive coated surface of backing 12 is not readily exposed to contamination.

Figure 3A:
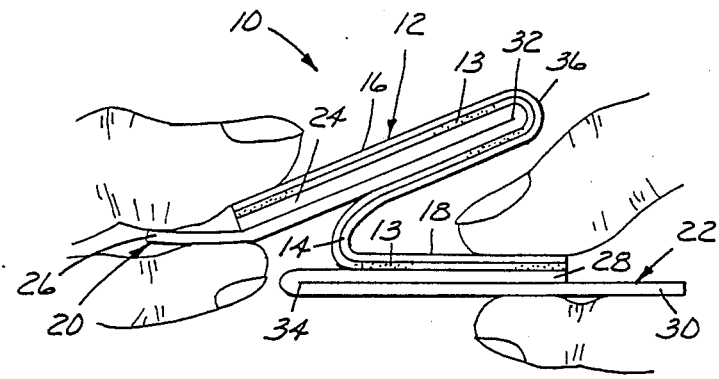
FIG. 3a is an edge view of the film dressing of FIG. 1 where the user is beginning to expose the center portion of the adhesive coated backing for application to the skin.
Figure 3B:
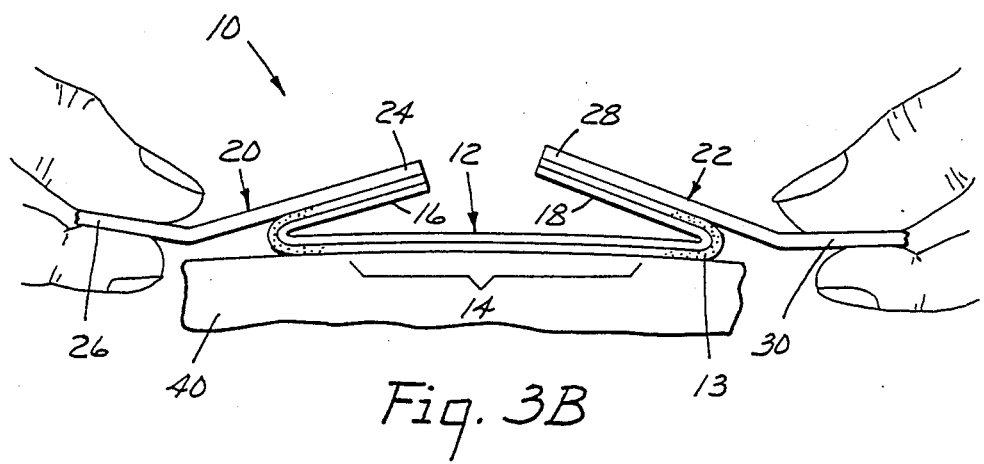
FIG. 3b is an edge view of the film dressing of FIG. 1 where the center portion of the adhesive coated backing is applied to the skin with the liner pieces continuing to be removed.
Figure 3C:
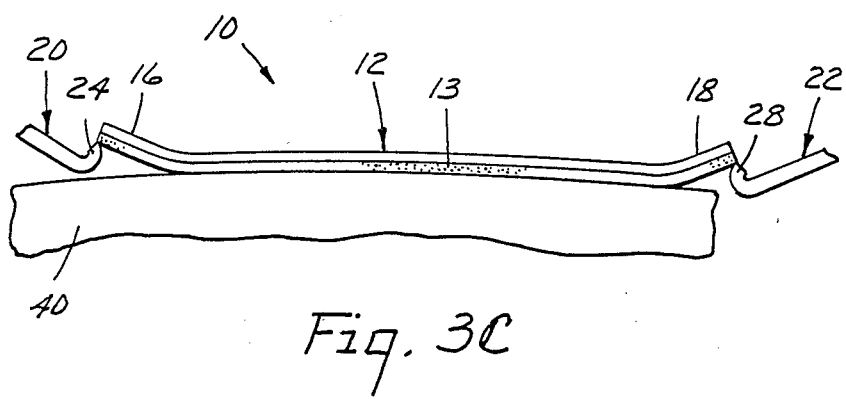
FIG. 3c is an edge view of the film dressing of FIG. 1 partially applied to the skin with the liner pieces almost completely removed.

FIGS. 3a, 3b and 3c show successive steps in application of composite 10 of this invention to the skin 40. As shown in FIG. 3a, the user grasps with one hand side region 16 of backing 12 together with upper portion 24 and lower portion 26 of first liner piece 20. With the other hand, the user grasps side region 18 of backing 12 together with upper portion 28 and lower portion 30 of second liner piece 22. The user then pulls in radially opposite directions, exposing the adhesive coated surface of center region 14 of backing 12.

As shown in FIG. 3b, center region 14 of backing 12 is applied to skin 40. The user grasps lower portion 26 of first liner piece 20 with one hand and lower portion 30 of second liner piece 22 with the other hand and pulls in radially opposite directions. Because lower portions 26 and 30 are separately grasped by the user at this step in application of dressing composite 10, lower portions 26 and 30 preferably extend beyond upper portions 24 and 28, respectively, for ease in gripping.

FIG. 3c shows dressing composite 10 with first liner piece 20 and second liner piece 22 almost completely removed. As the user pulls the lower portion 26 and lower portion 30 of the liner pieces in radially opposite directions, upper portion 24 and upper portion 28 are peeled away from the adhesive coated surface of side regions 16 and 18 of backing 12, which adhere to skin 40.

Figure 4:
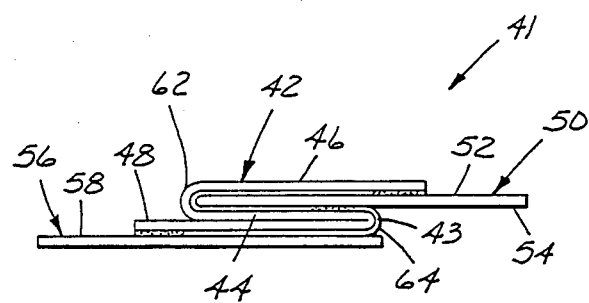
FIG. 4 is an edge view of an alternative embodiment of a film dressing according to the present invention.

FIG. 4 shows an end view of dressing composite 41, which is an alternative embodiment of the present invention having backing 42, pressure sensitive adhesive 43, first liner piece 50 and second liner piece 56. As in the previously shown embodiment, backing 42 contains center region 44 and side regions 46 and 48. The liner pieces in this embodiment, however, are single sheets that are not divided into portions. Top face 52 of first liner piece 50 is releasably adhered to side region 46 of backing 42. Top face 58 of second liner piece 56 is releasably adhered to side region 48 of backing 42. Backing 42 is folded at fold 62 so that center region 44 is releasably adhered to bottom face 54 of first liner piece 50. Backing 42 is then folded back onto itself at fold 64 so that the backing is in a generally Z-shaped configuration. Preferably, backing 42 is folded at fold 64 such that second liner piece 56 overhangs the adhesive coated surface of backing 42.

The dressing embodiment 41 of FIG. 4 is applied to the skin in much the same manner as the previously described embodiment. The user grasps the liner pieces 50 and 56 and pulls in radially opposite directions, exposing the adhesive coated surface of center region 44 of backing 42. After the adhesive coated surface of center region 44 is applied to the skin, liner pieces 50 and 56 are removed one by one by bending backing 42 so that the portion of liner piece 50 that is adjacent to center region 44 begins to peel away from backing 42. The backing is then rolled in a sliding motion into place on the skin, simultaneously removing first liner piece 50 while applying the adhesive coated backing 42 to the skin.

Although the ultimate delivery method of this invention requires that the backing of the composite be in a generally Z-shaped configuration as observed from an edge view, it is contemplated that these dressing composites may be provided to the user wherein the backing has only a single fold. This single fold is the above described firs fold wrapping the backing around the first liner piece. The user would then be instructed to fold the liner back onto itself in the Z configuration to allow delivery in the method as described above.

When the composite is provided in the generally Z-shaped configuration, the inclusion of additional means to assist the user in handling the composite is contemplated. For example, folded liner pieces may be temporarily held together by appropriate liner association means to avoid premature exposure of the adhesive coated side regions of the backing. A liner association means could be, for example, a spot of adhesive that temporarily fastens the upper portion of the liner piece to the lower portion of the liner piece. After application of the center region of the backing to the skin, the liner association means is easily overcome by either a separate motion to separate the liner portions or by simply pulling on the lower portion of the liner pieces as in the above described method of delivery.

In the foregoing description it will be understood that the use of the terms "fold", "folded" and the like are used for convenience in designated parts of the composite and the relative spatial configurations of these parts. It will be apparent that actual creases in the backing and liner are not required to obtain the composite of this invention. The presence of actual creases in the liner pieces is preferred in the folded liner piece embodiment.

The delivery system of the present invention is useful in connection with any backing having a pressure-sensitive adhesive coated on to it. Representative backings include non-woven fibrous webs, fibrous webs, knits, and other familiar backing materials. The preferred backing materials are polymeric films. The invention is particularly useful in pressure-sensitive adhesive composites having high moisture vapor permeable films. U.S. Pat. Nos. 3,645,835, and 595,001 both incorporated herein by reference, describe methods of making such a high vapor/moisture permeable film and methods for testing its permeability.

The film/adhesive composite should transmit moisture vapor at a rate of at least 300 g/m$^2$/24 hrs/37° C./100-10% RH. Preferably the adhesive coated film transmits moisture vapor at a rate of at least 700 g/m$^2$/24 hrs/37° C./100-10% RH.

The composite is preferably conformable to anatomical surfaces. This means that when the composite is applied to an animal anatomical surface it conforms to the surface even when the surface is moved. The preferred backings are also conformable to animal anatomical joints. When the joint is flexed and then returned to its unflexed position, the backing stretches to accommodate the flexion of the joint but is resilient enough to continue to conform to the joint when the joint is returned to its unflexed condition.

A measure of conformability is the "F" value, which is a measurement of force of elongation that is taken at a designated percent elongation point (identified by subscript) of a material. $F_{10}$ value as referred to herein is effectively determined using ASTM test method D 3759, except that the force measurements are taken at ten percent elongation. An Intelect II unit from Thwing-Albert Instrument Company (Philadelphia, PA) is used in this test procedure to obtain these values. The cross-head speed of the Intelect II is set at ten inches per minute and the chart speed is set at ten inches (25.4 cm) per minute. The gauge length is set at two inches (5.1 cm) with the test sample cut to test a one-inch width (2.54 cm).

The $F_{10}$ value gives an approximation of the motion of the body surface and ability of a material to stretch with these body deformations. The $F_{10}$ value for the backing should be no greater than about 1 pound (454 grams) and preferably less than about 0.8 pounds (363 grams). In the preferred embodiments of wound dressings and drapes, backings which have $F_{10}$ values upwards of 2.5 pounds (1135 grams) may be used. However, as the $F_{10}$ value increases, the conformability decreases and the ability of the backing to perform comfortably as medical dressings likewise decreases.

Conformability is also somewhat dependent on thickness, thus the thinner the backing the more conformable it is. Generally, the films are from 12 to 25 microns thick. Examples of polymers which are suitable for use as wound dressing films in the present invention include polyurethane such as Estane TM (B. F. Goodrich, Cleveland, Ohio), elastomeric polyester such as duPont Hytrel TM polyester elastomer (Wilmington, Del.), polyethylene, blends of polyurethane and polyester, chlorinated polyethylene, styrene/butadiene block copolymers such as Kraton TM brand thermoplastic rubber (Shell Chemical Company, Houston, Tex.), Pedax TM polyether block amides (distributed by Rilsan Corp., Glen Rock, N.J.), and polyvinyl chloride.

Particularly preferred backings are polyurethane and elastomeric polyester films. These films combine the desirable properties of resiliency, high moisture vapor permeability and transparency.

The preferred pressure-sensitive adhesives which can be used in the preferred wound dressing embodiment are the normal adhesives which are applied to the skin such as the acrylate copolymers described in U.S. Pat. No. Re. 24,906, particularly a 97:3 iso-octyl acrylate:acrylamide copolymer. Other useful adhesives are those described in U.S. Pat. No. 3,389,827, which discloses block copolymers having three or more polymer block structures having a general configuration -A-B-A- wherein each A block is a thermoplastic polymer with a glass transition temperature above room temperature (i.e., above about 20° C.) having an average molecular weight between about 5000 and 125,000 and the B block is a polymer of a conjugated diene having an average molecular weight between about 15,000 and 250,000. Additional examples of useful adhesives are iso-octyl acrylate/n-vinyl pyrrolidone copolymer adhesives and crosslinked acrylate adhesives such as, for example, those described in U.S. Pat. No. 4,112,213. Inclusion of medicaments or antimicrobial agents such as iodine in the adhesive is useful for enhancing wound healing and preventing infection. U.S. Pat. Nos. 4,310,509 and 4,323,557 describe such antimicrobial adhesives.

Examples of liners suitable for use in the present invention are liners made of kraft papers, polyethylene, polypropylene, polyester or composites of any of these materials. These liners are coated with release agents such as fluorochemicals or silicone. U.S. Pat. No. 4,472,480 describes low surface energy perfluorochemical liners. The preferred liners are papers, polyolefin films, or polyester films coated with silicone release materials. Examples of the silicone coated release papers are Polyslik TM silicone release papers supplied by James River Co., H. P. Smith Division (Bedford Park, Ill.), and silicone coated papers supplied by Daubert Chemical Co.(Dixon, Ill.). The preferred liner is 1-60BKG-157 paper available from Daubert, which is a super calendered kraft paper with a water based silicone surface.

Other combinations of adhesives and liners are feasible. Those skilled in the art are familiar with processes of testing a new adhesive against different liners or a new liner against different adhesives in order to arrive at the combination of qualities desired in the final product. Handbook of Pressure-Sensitive Adhesive Technology, Chapter 18 "Silicone Release Coatings" Van Nostrand-Reinhold, 1982, pp. 384–403 describes the considerations pertinent to selection of a silicone release liner. U.S. Pat. No. 4,472,480 describes considerations pertinent to selection of a perfluoropolyether release liner. In the preferred wound dressing embodiment of the present invention, the choice of adhesive is limited to those that are safe to use on skin, and preferably to those that are of the class known as hypoallergenic. The preferred acrylate copolymers are adhesives of this class. Liners are available from a variety of manufacturers in a wide variety of proprietary formulations. One normally tests these in simulated use conditions against an adhesive of choice to arrive at a product with the desired release characteristics.

The composite of the present invention may be made by conventional techniques (e.g., extrusion, solvent casting, calendering, and laminating and the like) which are familiar to those skilled in the art. (See Modern Plastics Encyclopedia McGraw Hill, 1984-85; Coating and Laminating Machines, Weiss Coverting Technology Co., 1977.) The method of making a composite is further exemplified by the following non-limiting examples.

EXAMPLE 1

A 28 micron thick polyurethane film backing measuring 6 cm. × 7 cm. is coated on one surface with a pressure sensitive adhesive at a coating weight of approximately 460 mg/200 sq. cm. The adhesive is a copolymer of approximately 96 parts iso-octyl acrylate and approximately 4 parts of acrylamide.

Two pieces of silicone-coated release liner material, 2-60kg-157/99am, manufactured by Daubert Coated Products, Dixon, Ill., measuring 5.7 × 6 cm. are folded (157 silicone-coated surface out) so that the upper portions measure 2.6 × 6 cm. and the lower portions measure 3.1 × 6 cm. The 157 silicone-coated surfaces of the upper portions of these liner pieces are releasably adhered to the adhesive-coated side regions of the backing, leaving a gap of about 180 mm. at the center of the backing. These liner pieces are oriented on the backing so that the folds abut the center region of the backing. The backing is then wrapped around the fold in the first liner piece, so that the adhesive on the center region of the film is releasably adhered to the silicone-coated surface of the lower portion of the first liner piece. At a line in the backing corresponding to the fold in the second liner piece, the backing is folded back onto itself in substantially a "Z" configuration so that the non-adhesive coated surface of the center region of the backing contacts or is otherwise proximate to the non-adhesive coated surface of one of the side regions of the backing.

EXAMPLE 2

A 28 micron thick polyurethane film backing measuring 10 cm. × 12 cm. is coated on one surface with a pressure sensitive adhesive at a coating weight of approximately 460 mg/200 sq. cm. The adhesive is a copolymer of approximately 96 parts iso-octyl acrylate and approximately 4 parts of acrylamide.

Two pieces of silicone-coated release liner material, 2-60kg-157/99am, manufactured by Daubert Coated Products, Dixon, Ill., measuring 10 × 10 cm. are folded (157 silicon-coated surface out) so that the upper portions measure 4.25 × 10 cm. and the lower portions measure 5.75 × 10 cm. The 157 silicone-coated surfaces of the upper portions of these liner pieces are releasably adhered to the adhesive-coated side regions of the backing, leaving a gap of about 350 mm. at the center of the backing. These liner pieces are oriented on the backing so that the folds abut the center region of the backing. The backing is then wrapped around the fold in the first liner piece, so that the adhesive on the center region of the backing is releasably adhered to the silicone-coated surface of the lower portion of the first liner piece. At a line in the backing corresponding to the fold in the second liner piece, the backing is folded back onto itself in substantially a "Z" configuration so that the non-adhesive coated surface of the center region of the backing contacts or is otherwise proximate to the non-adhesive coated surface of one of the side regions of the backing.

EXAMPLE 3

A 28 micron thick polyurethane film measuring 6 cm. × 7 cm. is coated on one surface with a pressure sensitive adhesive at a coating weight of approximately 460 mg/200 sq. cm. The adhesive is a copolymer of approximately 96 parts iso-octyl acrylate and approximately 4 parts of acrylamide.

Two liner pieces of polyethylene material (commercially available as 77-5-HiD-S253D-BLUE from Mead Release Products, West Chicago, Ill.) are prepared by adhering two upper portions measuring 2.6 × 6 cm. respectively to two lower portions measuring 3.1 × 6 cm. along one edge using 3M Scotch Brand Double Stick Tape, Cat. No. 136, having a width of about 1.25 cm. The outwardly facing surfaces of the upper portions of these liner pieces are releasably adhered to the adhesive-coated side regions of the backing, leaving a gap of about 180 mm. at the center of the backing. These liner pieces are oriented on the backing so that the folds abut the center region of the backing. The backing is then wrapped around the edge of the first liner piece, so that the adhesive on the center region of the film is releasably adhered to the outwardly facing surface of the lower portion of the first liner piece. At a line in the backing corresponding to the fold in the second liner piece, the backing is folded back onto itself in substantially a "Z" configuration so that the non-adhesive coated surface of the center region of the backing contacts or is otherwise proximate to the non-adhesive coated surface of one of the side regions of the backing.

EXAMPLE 4

A 28 micron thick polyurethane film backing measuring 6 cm. × 7 cm. is coated on one surface with a pressure sensitive adhesive at a coating weight of approximately 460 mg/200 sq. cm. The adhesive is a copolymer of approximately 96 parts iso-octyl acrylate and approximately 4 parts of acrylamide.

Two pieces of silicone-coated release liner material, 2-60 kg-157/99 am, manufactured by Daubert Coated Products, Dixon, Ill., each measuring 5.7 × 6 cm. are folded (157 silicone-coated surface out) so that the upper portions measure 2.6 × 6 cm. and the lower portions measure 3.1 × 6 cm. The 157 silicone-coated surfaces of the upper portions of these liner pieces are releasably adhered to the adhesive-coated side regions of the backing, leaving a gap of about 180 mm. at the center of the backing. These liner pieces are oriented on the backing so that the folds abut the center region of the backing. The backing is then wrapped around the fold in the first liner piece, releasably adhering about one half of the center region of the film to the silicone-coated surface of the lower portion of the first liner piece. The backing is folded back against itself and the remaining exposed half of the center region of the backing is releasably adhered to the silicone-coated surface of the lower portion of the second liner piece while at the same time wrapping the backing around the fold in the first liner piece. Thus, in this embodiment the backing, when viewed from an edge view, is in a "W" configuration.

EXAMPLE 5

A 28 micron thick polyurethane film backing measuring 6 cm. × 7 cm. is coated on one surface with a pressure sensitive adhesive at a coating weight of approximately 460 mg/200 sq. cm. The adhesive is a copolymer of approximately 96 parts iso-octyl arcylate and approximately 4 parts of acrylamide.

Two pieces of polystyrene release liner material, 2-6 polystyrene-393, manufactured by Daubert Coated Products, Dixon, Ill., measuring 3.1 × 6 cm. are releasably adhered to the adhesive coated side regions of the backing, leaving a gap of about 180 mm. at the center of the backing. For purposes of clarity in this description, the liner pieces are releasably adhered to the side regions of the backing at the top face of the liner piece. The backing is then wrapped around the first liner piece, so that the adhesive on the center region of the film is releasably adhered to the bottom face of the first liner piece. At a line in the backing corresponding to the edge in the second liner piece, the backing is folded back onto itself in substantially a "Z" configuration so that the non-adhesive coated surface of the center region of the backing contacts or is otherwise proximate to the non-adhesive coated surface of one of the side regions of the backing.

The foregoing description has been directed to particular preferred embodiments for purposes of illustration and explanation. Those skilled in the art will appreciate that many modifications will be possible without departing from the spirit of the invention. For example, the composite may further comprise an absorbent pad or adhesive voids to increase moisture vapor transmission.

I claim:

1. An adhesive composite comprising a backing having a coating of pressure-sensitive adhesive on one surface, said backing having a center region and two side regions adjacent said center region, and further comprising first and second liner pieces, wherein said first liner piece is releasably adhered to the adhesive coated surface of one of the side regions of the backing and said second liner piece is releasably adhered to the adhesive coated surface of the other side region of the backing, and wherein said backing is wrapped around the first liner piece, releasably adhering said adhesive coated surface of the center region of the backing to at least one of the liner pieces.

2. The adhesive composite of claim 1 wherein each liner piece has an upper portion and a lower portion joined together along one edge, wherein one of the side regions of the backing is releasably adhered to the outward facing surface of the upper portion of the first liner piece and the other side region of the backing is releasably adhered to the outward facing surface of the upper portion of the second liner piece, and the backing is folded so that the backing is wrapped around the first liner piece and the center region of the backing is releasably adhered to the outward facing surface of the lower portion of at least one of the liner pieces.

3. An adhesive composite of claim 2 wherein the upper and lower portions of the liner pieces are formed by folding the liner pieces.

4. The adhesive composite of claim 2 wherein the upper and lower portions of the liner pieces are formed by adhering two separate liner pieces.

5. The adhesive composite of claim 2 wherein the center region of the backing comprises less than one-third of the total area of the backing.

6. The adhesive composite of claim 2 wherein the backing is folded once.

7. The adhesive composite of claim 2 wherein the backing contains two folds such that the non-adhesive coated surface of the center region of the backing contacts or is proximate to the non-adhesive coated surface of one of the side regions of the backing.

8. The adhesive composite of claim 7 wherein the total area of the center region of the backing is less than the total area of each of the side regions of the backing.

9. The adhesive composite of claim 2 wherein the lower portion of each of the liner pieces is longer than the upper portion of each of the liner pieces.

10. The adhesive composite of claim 2 wherein the backing consists of polyurethane or polyester.

11. The adhesive composite of claim 10 wherein the composite is a dressing that transmits moisture vapor at a rate of at least 300 g/m$^2$/24 hrs./37° C./100–10% RH.

12. The adhesive composite of claim 1 wherein said first and second liner pieces have top and bottom faces, and wherein one of the side regions of the backing is releasably adhered to the top face of the first liner piece and the other side region of the backing is releasably adhered to the top face of the second liner piece, and the backing is folded so that the center region of the backing is releasably adhered to the bottom face of at least one of the liner pieces.

13. The adhesive composite of claim 12 wherein the center region of the backing comprises less than one-third of the total area of the backing.

14. The adhesive composite of claim 12 wherein the backing is folded once.

15. The adhesive composite of claim 12 wherein the backing contains two folds such that the non-adhesive coated surface of the center region of the backing contacts or is proximate to one of the non-adhesive coated surfaces of the side regions of the backing.

16. The adhesive composite of claim 13 wherein the total area of the center region is less than the total area of each of the side regions.

17. The adhesive composite of claim 12 wherein the backing consists of polyurethane or polyester.

18. The adhesive composite of claim 17 wherein the composite is a dressing that transmits moisture vapor at a rate of at least 300 g/m$^2$/24 hrs./37°/100–10% RH.

19. The adhesive composite of claim 1 wherein the backing is folded a first time so that the backing is wrapped around the first liner piece and the center region of the backing is releasably adhered to at least one of the liner pieces, and the backing is folded a second time so that the non-adhesive coated surface of the center region of the backing contacts or is proximate to the non-adhesive coated surface of one of the side regions of the backing.

* * * * *

UNITED STATES PATENT AND TRADEMARK OFFICE
CERTIFICATE OF CORRECTION

PATENT NO. : 4,917,928

DATED : April 17, 1990

INVENTOR(S) : Steven B. Heinecke

It is certified that error appears in the above-identified patent and that said Letters Patent is hereby corrected as shown below:

Col. 4, line 67, "firs" should be -- first -- .

Col. 5, line 34, "595,001" should be -- 4,595,001 -- .

Signed and Sealed this

Fifteenth Day of December, 1992

*Attest:*

DOUGLAS B. COMER

*Attesting Officer*  Acting Commissioner of Patents and Trademarks